United States Patent [19]
Yoon

[11] Patent Number: 5,843,017
[45] Date of Patent: Dec. 1, 1998

[54] MULTIFUNCTIONAL TISSUE DISSECTING INSTRUMENT

[76] Inventor: InBae Yoon, 2101 Highland Ridge Dr., Phoenix, Md. 21131

[21] Appl. No.: 670,188

[22] Filed: Jun. 21, 1996

Related U.S. Application Data

[60] Continuation-in-part of Ser. No. 295,032, Aug. 25, 1994, Pat. No. 5,599,292, which is a division of Ser. No. 130,484, Oct. 1, 1993, Pat. No. 5,484,426, which is a division of Ser. No. 600,775, Oct. 23, 1990, Pat. No. 5,374,261, which is a continuation-in-part of Ser. No. 556,081, Jul. 24, 1990, Pat. No. 5,074,840.

[51] Int. Cl.[6] .............................. A61B 17/20; A61B 17/00
[52] U.S. Cl. ................................ 604/22; 601/1; 601/170; 601/264; 606/190; 600/564
[58] Field of Search .......................... 604/1–3, 11, 22, 604/93, 158, 170, 264, 284; 606/190; 128/749, 750, 751, 752; 600/562–565

[56] References Cited

U.S. PATENT DOCUMENTS

| | | |
|---|---|---|
| 682,090 | 9/1901 | Lee . |
| 716,040 | 12/1902 | Holt . |
| 1,114,268 | 10/1914 | Kells . |
| 1,523,943 | 1/1925 | Fowle . |
| 1,562,656 | 11/1925 | Park . |
| 1,909,967 | 5/1933 | Jones . |
| 3,495,917 | 2/1970 | Truhan ........................................ 604/2 |
| 3,519,364 | 7/1970 | Truhan ........................................ 604/2 |
| 3,882,852 | 5/1975 | Sinnreich . |
| 3,978,863 | 9/1976 | Fettel et al. . |
| 3,996,938 | 12/1976 | Clark, III . |
| 4,023,559 | 5/1977 | Gaskell . |
| 4,198,981 | 4/1980 | Sinnreich . |
| 4,329,990 | 5/1982 | Sneider ........................................ 604/2 |
| 4,533,356 | 8/1985 | Bengmark et al. . |
| 4,568,326 | 2/1986 | Rangaswamy . |
| 4,921,484 | 5/1990 | Hillstead . |
| 4,969,890 | 11/1990 | Sugita et al. . |
| 4,990,152 | 2/1991 | Yoon . |
| 4,993,412 | 2/1991 | Murphy-Chutorian . |
| 5,002,556 | 3/1991 | Ishida et al. . |
| 5,030,227 | 7/1991 | Rosenbluth et al. . |
| 5,074,840 | 12/1991 | Yoon . |
| 5,151,094 | 9/1992 | Hanifl . |
| 5,188,630 | 2/1993 | Christoudias . |

(List continued on next page.)

FOREIGN PATENT DOCUMENTS

| | | |
|---|---|---|
| 2848 | of 1907 | United Kingdom . |
| 2006019 | 5/1979 | United Kingdom . |
| WO86/06611 | 11/1986 | WIPO . |

*Primary Examiner*—John G. Weiss
*Assistant Examiner*—Dennis Ruhl

[57] ABSTRACT

A multifunctional tissue dissecting instrument for use in a surgical procedure includes a blunt dissector, a probe disposed within the blunt dissector and a handle coupled with the probe at a proximal end of the blunt dissector and operable to move a tip of the probe between a retracted position within the blunt dissector and an extended position protruding from the blunt dissector. The blunt dissector preferably includes an elongate tubular member and an absorbent body of material disposed on the distal end of the tubular member. The absorbent body at the distal end of the tubular member is configured to contact tissue for blunt dissection and, when other functions are desired or required as part of the surgical procedure, the probe tip can be moved from the retracted position to the extended position, for example to cut or penetrate tissue for sharp dissection, to transmit energy, to manipulate or pull the tissue or to otherwise treat the tissue. The body of absorbent material can also be used to absorb body fluids at the operative site and, if an operating channel is defined through the instrument in communication with the absorbent body, the operating channel can be used to provide fluid for irrigation, to create suction for aspiration and to administer medicaments at the operative site. Furthermore, the probe can be made hollow to define an operating channel through the instrument through which additional instruments can be introduced at the operative site or through which the functions of irrigating, aspirating and administering medicaments can be performed.

37 Claims, 5 Drawing Sheets

U.S. PATENT DOCUMENTS

| | | |
|---|---|---|
| 5,203,767 | 4/1993 | Cloyd . |
| 5,269,753 | 12/1993 | Wilk . |
| 5,273,524 | 12/1993 | Fox et al. .................................. 604/22 |
| 5,295,952 | 3/1994 | Pietrafitta . |
| 5,308,316 | 5/1994 | Williams et al. . |
| 5,310,407 | 5/1994 | Casale . |
| 5,342,390 | 8/1994 | Slater et al. ............................ 128/749 |
| 5,374,261 | 12/1994 | Yoon . |
| 5,385,570 | 1/1995 | Chin et al. .............................. 128/751 |
| 5,392,787 | 2/1995 | Yoon . |
| 5,399,161 | 3/1995 | Williams et al. . |
| 5,407,423 | 4/1995 | Yoon . |
| 5,415,634 | 5/1995 | Churinetz et al. . |
| 5,439,457 | 8/1995 | Yoon . |
| 5,451,204 | 9/1995 | Yoon . |
| 5,453,078 | 9/1995 | Valentine et al. . |
| 5,460,621 | 10/1995 | Gertzman et al. . |
| 5,466,231 | 11/1995 | Cercone et al. . |
| 5,484,426 | 1/1996 | Yoon . |
| 5,490,836 | 2/1996 | Desai . |
| 5,620,459 | 4/1997 | Lichtman ................................. 128/751 |

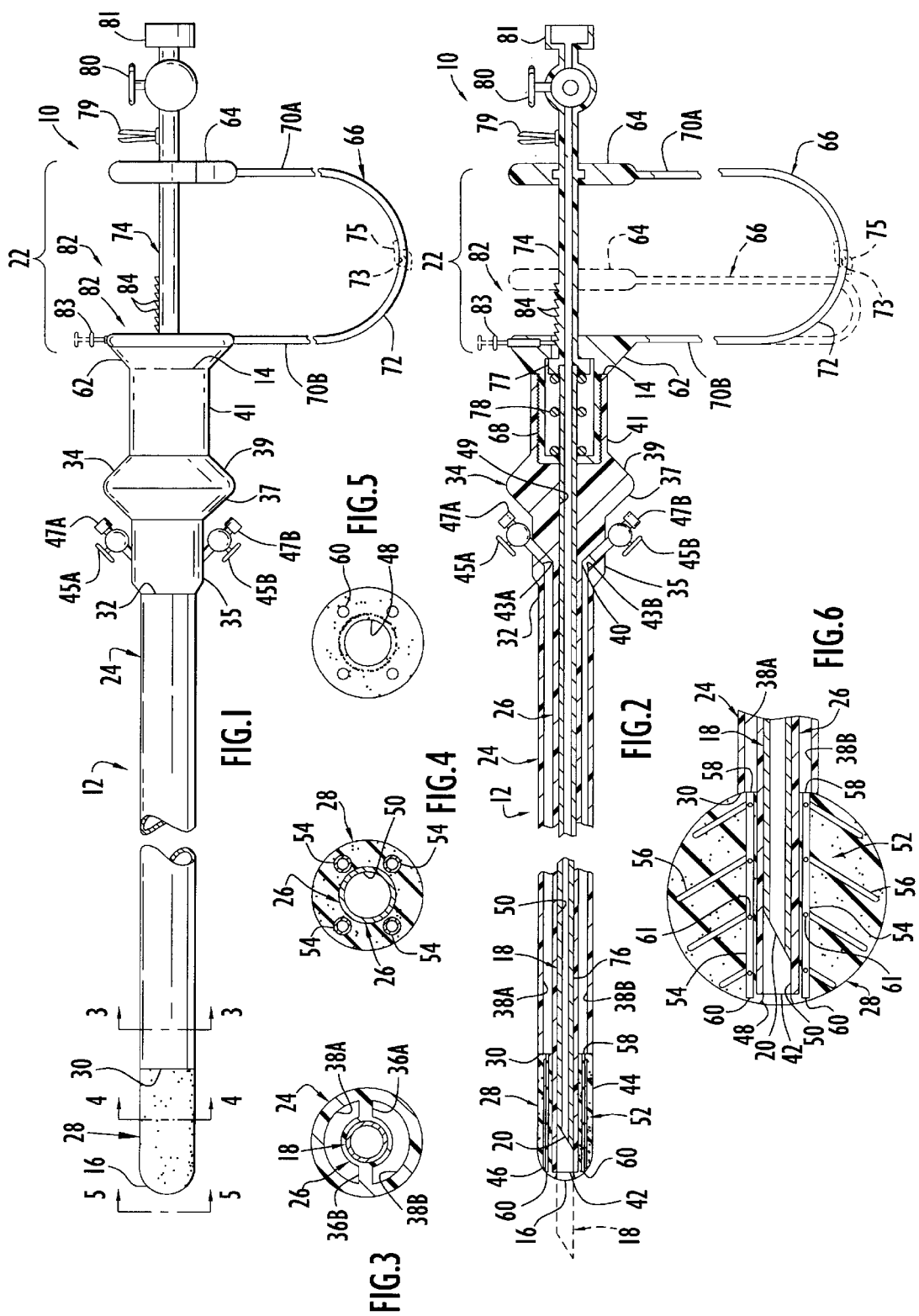

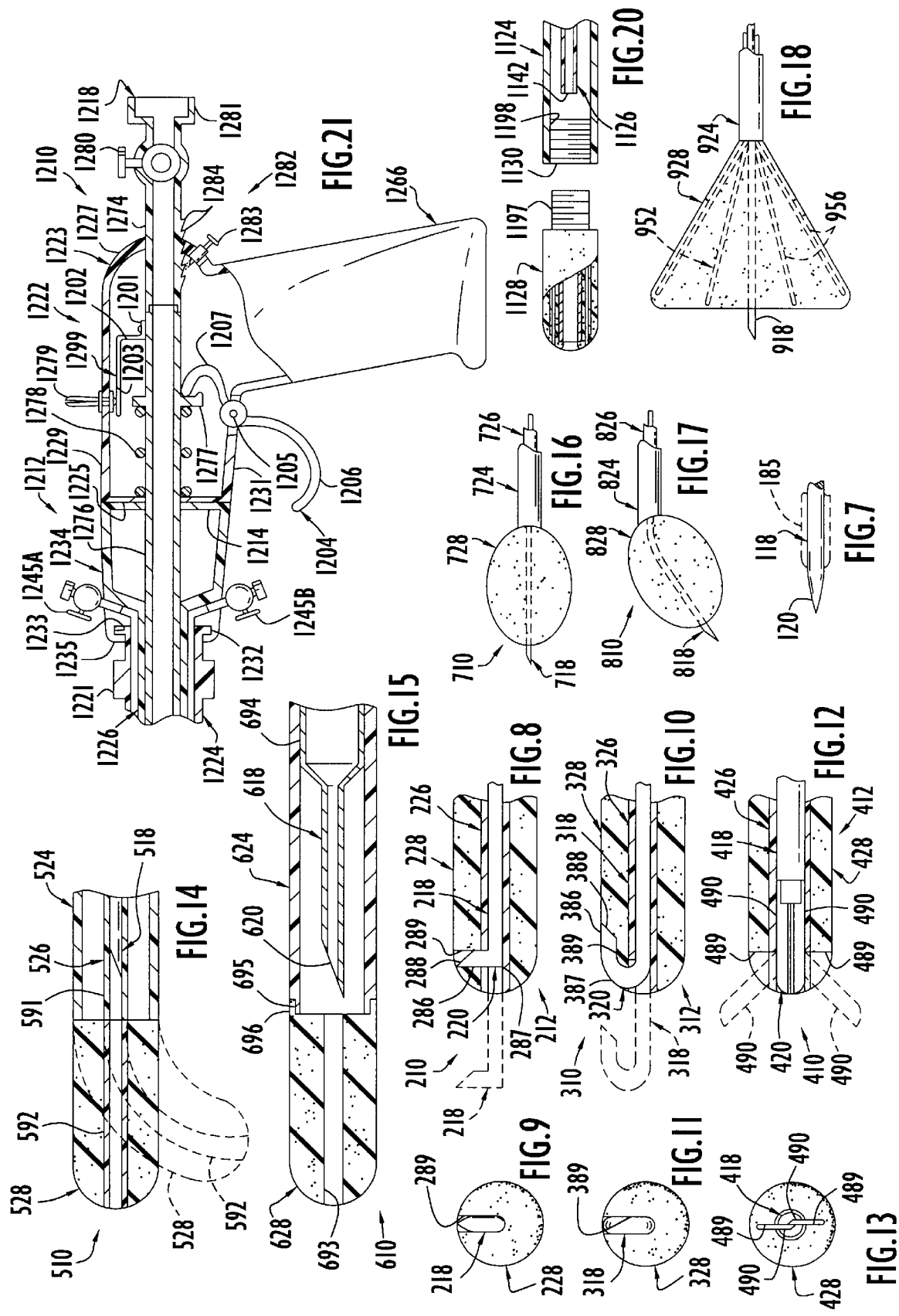

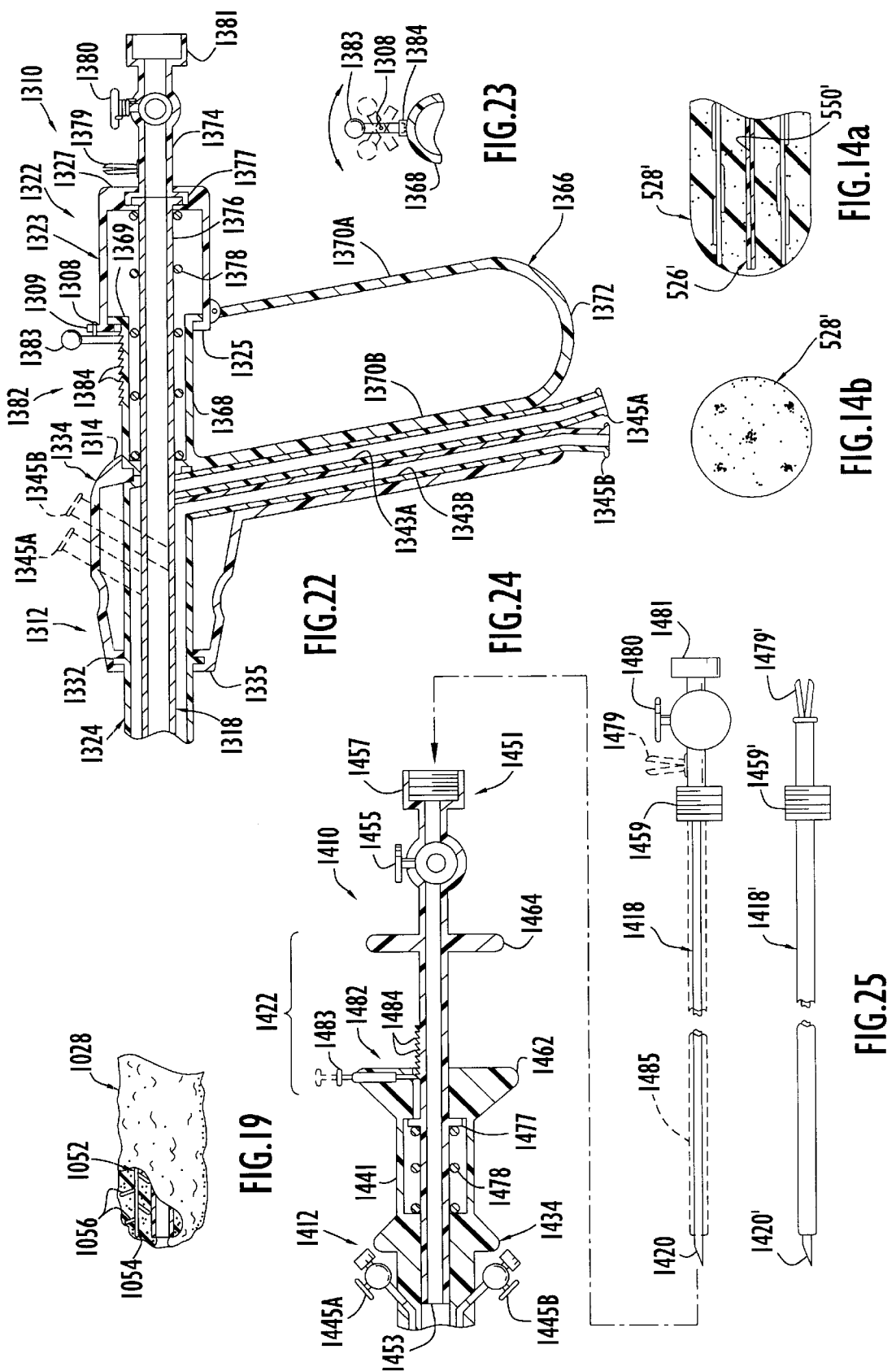

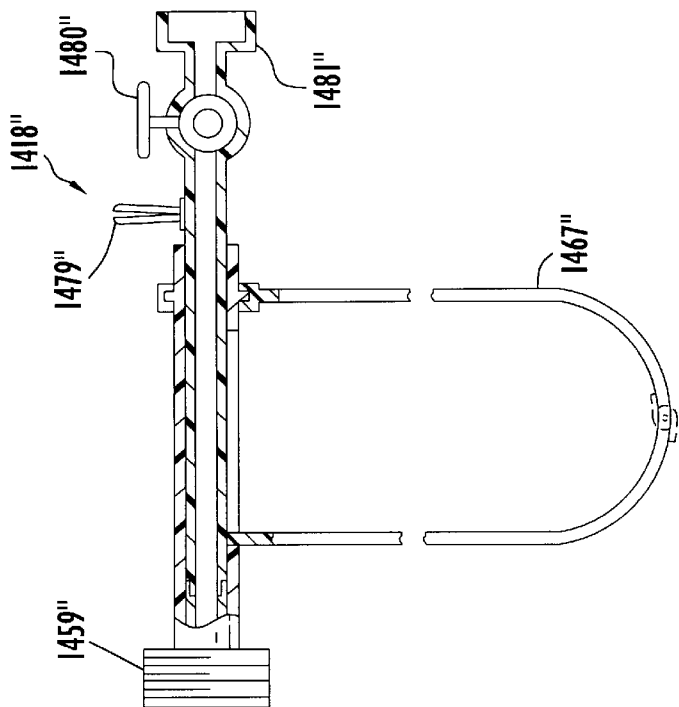
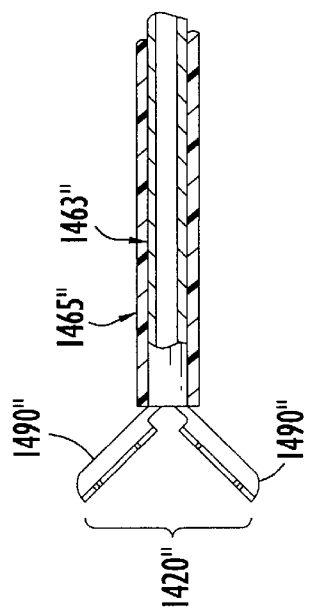
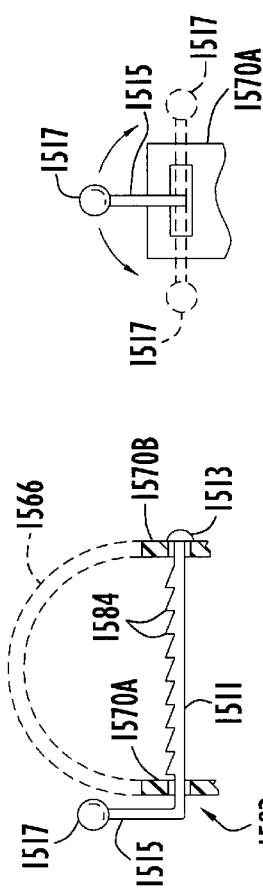
FIG.26
FIG.27
FIG.28

MULTIFUNCTIONAL TISSUE DISSECTING INSTRUMENT

CROSS-REFERENCE TO RELATED APPLICATIONS

This application is a continuation-in-part of application Ser. No. 08/295,032, filed Aug. 25, 1994, now U.S. Pat. No. 5,599,292, which is a division of application Ser. No. 08/130,484, filed Oct. 1, 1993, now U.S. Pat. No. 5,484,426, which is a division of application Ser. No. 07/600,775, filed Oct. 23, 1990, now U.S. Pat. No. 5,374,261, which is a continuation-in-part of application Ser. No. 07/556,081, filed Jul. 24, 1990, now U.S. Pat. No. 5,074,840. The disclosures in the above-mentioned patent applications are incorporated herein by reference.

BACKGROUND OF THE INVENTION

1. Field of the Invention

The present invention relates to medical procedures and instruments and, more particularly, to a multifunctional tissue dissecting instrument having a dissector body at a distal end for non-traumatically contacting anatomical tissue and one or more operating channels or passages formed therethrough for irrigating and aspirating, administering medicaments and introducing other instruments such as probes at the operative site.

2. Discussion of the Related Art

Endoscopic and minimally invasive medical procedures, such as laparoscopy, have become widely accepted for surgery and diagnosis due to the associated advantages relating to reduced trauma and hospitalization time. The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, ligating appliers, forceps, cauteries and the like into the anatomical cavity.

Endoscopic procedures commonly involve performing a number of individual acts or functions within the anatomical cavity including dissecting anatomical tissue in the cavity by separating the tissue along natural or created lines, manipulating and retracting tissue, separating adhering tissue (lysis of adhesion), penetrating or cutting tissue, transmitting energy to tissue, illuminating, visualizing, supplying fluid to irrigate, creating suction to aspirate and administering medicaments. In the past, blunt dissectors including absorbent bodies formed of sponge-like materials or gauze have been used endoscopically to absorb body fluids and to manipulate or dissect tissue and light adhesions in the body while other instruments or probes, such as needles, scissors and cauteries, have been used to perform functions such as penetrating, cutting and cauterizing tissue, requiring several incisions for placement of multiple portal sleeves to accommodate a suitable number of endoscopic instruments for performing the required functions or necessitating frequent withdrawal and replacement of individual endoscopic instruments through a single portal sleeve. While it is generally desirable to minimize the number of incisions created for performing a particular endoscopic procedure, substitution of instruments through a single incision can be time consuming depending on the efficiency of the medical facility and staff, increasing the period of anesthetization for the patient. Additionally, internal bleeding can develop during the substitution of instruments thereby obscuring the field of view and requiring time consuming cleanup procedures to be performed.

SUMMARY OF THE INVENTION

Accordingly, it is a primary object of the present invention to overcome the above-mentioned disadvantages of the prior art with a tissue dissecting instrument capable of performing multiple functions.

Another object of the present invention is to perform multiple functions through a single portal with a tissue dissecting instrument having a blunt dissector with a dissector body at a distal end, a probe disposed within the blunt dissector, and a handle operable to move a tip of the probe from a retracted position within the blunt dissector to an extended position protruding from the blunt dissector.

A further object of the present invention is to perform multiple functions through a single portal by operating a handle with one hand to move the tip of a probe from a retracted position within a blunt dissector to an extended position protruding from the blunt dissector.

It is another object of the present invention to increase the safety of surgical procedures performed through a portal by biasing the tip of a probe in a multifunctional tissue dissecting instrument toward a retracted position within a blunt dissector.

Still a further object of the present invention is to allow the user of a multifunctional tissue dissecting instrument to maintain the tip of a probe in an extended position relative to a blunt dissector by providing a locking mechanism which is selectively operable to prevent proximal movement of the probe relative to the blunt dissector.

The present invention has an additional object to perform multiple functions through a single portal with a tissue dissecting instrument having an absorbent body at a distal end for contacting anatomical tissue and an operating passage or channel formed therein for performing irrigation and aspiration, administering medicaments and introducing other instruments such as probes at the operative site.

Some of the advantages of the present invention over the prior art are that the tissue dissecting instrument can perform multiple functions through a single portal thereby minimizing the number of portals required to perform an endoscopic or vascular procedure, that the frequency of substitution of instruments through a single portal can be reduced, that single-handed operation of a blunt dissector and a probe is facilitated, that conventional handle structures can be used to provide users with a familiar feel and to decrease adaptation time, and that the entire instrument or components thereof can be sterilized for reuse or disposable for single-patient use as desired.

The present invention is generally characterized in a multifunctional tissue dissecting instrument for use in surgical procedures including a blunt dissector, a probe disposed in the blunt dissector and a handle coupled with the probe and operable to move a tip of the probe between a retracted position disposed within the blunt dissector and an extended position protruding from the blunt dissector. With the probe tip in the retracted position, the multifunctional instrument can be used as a blunt dissector to contact anatomical tissue for dissection. With the probe tip in the extended position, the tip of the probe can be used to treat anatomical tissue. In a preferred embodiment, the blunt dissector includes an elongate tubular member with a dissector body (e.g., an absorbent body of material) on a distal end thereof, and the probe is disposed within the elongate tubular member and coupled with the handle at the proximal end of the elongate tubular member. The probe can be biased proximally relative to the blunt dissector so that, when the handle is released, the probe tip will automatically return to the retracted position. For prolonged use of the probe tip, a locking mechanism can be provided to prevent proximal movement of the probe relative to the blunt dissector. The probe can be solid but is preferably hollow to define an operating channel through the instrument through which additional instruments can be inserted and/or fluids transported to irrigate, aspirate or administer medicaments at the operative site. The tip of the probe can have any configuration to assist in performing an endoscopic procedure including, but not limited to, needle-like configurations, hook-like configurations, scissor-like configurations and configurations useful in electrosurgery.

Another aspect of the present invention is generally characterized in a multifunctional tissue dissecting instrument for use in surgical procedures including an elongate tubular member having a distal end adapted to be introduced into an anatomical cavity through a portal and a proximal end adapted to be positioned externally of the anatomical cavity, and an absorbent body of material disposed at the distal end of the elongate tubular member to absorb body fluids at the operative site and to contact anatomical tissue for blunt dissection. One or more operating channels extend through the elongate tubular member to provide access to the operative site in the anatomical cavity, either directly or via the absorbent body. In a preferred embodiment, a tubular member or spine is disposed in the absorbent body and communicated with an operating channel in the elongate tubular member to supply fluid for irrigation, create suction for aspiration, administer medicaments or introduce instruments at the operative site. The multifunctional instrument can optionally be provided with a hub mounting one or more valves with couplings for communicating fluid sources, sources of suction, medicaments and instruments with operating channels in the elongate tubular member.

A further aspect of the present invention is generally characterized in a method of performing a surgical procedure including the steps of establishing a portal through a wall of an anatomical cavity to provide access to an operative site in the anatomical cavity, introducing an instrument at the operative site through the portal, the instrument including a blunt dissector with an absorbent body of material at a distal end and a probe disposed within the blunt dissector, extending a tip of the probe from a protected position within the blunt dissector to an extended position protruding from a distal end of the blunt dissector, using the tip of the probe to treat tissue at the operative site, and causing the tip of the probe to move proximally to the protected position within the blunt dissector. With the probe in the retracted position, the blunt dissector can be used to absorb body fluids and/or to dissect anatomical tissue at the operative site. With the probe tip in the extended position, the instrument can be used to treat anatomical tissue, for example by using the probe tip to perform sharp dissection, to manipulate the tissue, or to transmit energy to the tissue. Furthermore, if the probe is hollow, an operating channel can be defined therethrough and additional instruments can be introduced at the operative site through the operating channel or fluids transmitted to perform at least one of the functions of irrigating, aspirating and administering medicaments at the operative site.

Other objects and advantages of the present invention will become apparent from the following description of the preferred embodiments taken in conjunction with the accompanying drawings, wherein like parts in each of the several figures are identified by like reference numerals or by reference numerals having the same last two digits.

BRIEF DESCRIPTION OF THE DRAWINGS

FIG. 1 is a side view, in broken longitudinal elevation, of a multifunctional tissue dissecting instrument according to the present invention.

FIG. 2 is a side view, in broken longitudinal section, of the multifunctional tissue dissecting instrument of FIG. 1.

FIG. 3 is a cross-sectional view of the multifunctional tissue dissecting instrument of FIG. 1 taken through line 3—3.

FIG. 4 is a cross-sectional view of the multifunctional tissue dissecting instrument of FIG. 1 taken through line 4—4.

FIG. 5 is a front view of the multifunctional tissue dissecting instrument of FIG. 1 taken through line 5—5.

FIG. 6 is a fragmentary side view, partly in section, illustrating the body of absorbent material at the distal end of the multifunctional tissue dissecting instrument of FIG. 1 in an expanded state.

FIG. 7 is a fragmentary side view, in elevation, of a modified probe for use with the multifunctional tissue dissecting instrument according to the present invention.

FIGS. 8 and 9 are a fragmentary sectional side view and a front view, respectively, of a modified probe and distal end configuration for the multifunctional tissue dissecting instrument according to the present invention.

FIGS. 10 and 11 are a fragmentary sectional side view and a front view, respectively, of a modified probe and distal end configuration for the multifunctional tissue dissecting instrument according to the present invention.

FIGS. 12 and 13 are a fragmentary sectional side view and a front view, respectively, of a modified probe and distal end configuration for the multifunctional tissue dissecting instrument according to the present invention.

FIG. 14 is a fragmentary side view, partly in section, illustrating a modified distal end configuration for the multifunctional tissue dissecting instrument according to the present invention.

FIGS. 14A and 14B are a fragmentary sectional side view and a front view, respectively, of a modified distal end configuration for the multifunctional tissue dissecting instrument according to the present invention.

FIG. 15 is a fragmentary side view, partly in section, illustrating a modified probe and distal end configuration for the multifunctional tissue dissecting instrument according to the present invention.

FIG. 16 is a fragmentary side view of a modified distal end configuration for the multifunctional tissue dissecting instrument according to the present invention.

FIG. 17 is a fragmentary side view of a modified distal end configuration for the multifunctional tissue dissecting instrument according to the present invention.

FIG. 18 is a fragmentary side view of a modified distal end configuration for the multifunctional tissue dissecting instrument according to the present invention.

FIG. 19 is a fragmentary side view, partly in section, of a modified distal end configuration for the multifunctional tissue dissecting instrument according to the present invention.

FIG. 20 is an exploded side view, partly in section, showing a detachable distal end configuration for the multifunctional tissue dissecting instrument according to the present invention.

FIG. 21 is a fragmentary side view, partly in section, illustrating a modified handle for use with multifunctional tissue dissecting instrument according to the present invention.

FIG. 22 is a fragmentary side view, partly in section, illustrating another modified handle for use with multifunctional tissue dissecting instrument according to the present invention.

FIG. 23 is a fragmentary sectional view of the locking mechanism shown in FIG. 22.

FIG. 24 is a fragmentary side view, partly in section, of a modified handle and probe for use with the multifunctional tissue dissecting instrument according to the present invention.

FIG. 25 is a side view, in broken longitudinal elevation, illustrating a modified probe for use with the multifunctional tissue dissecting instrument shown in FIG. 22.

FIG. 26 is a side view, in broken longitudinal elevation, illustrating another modified probe for use with the multifunctional tissue dissecting instrument shown in FIG. 22.

FIGS. 27 and 28 are a fragmentary side view and a fragmentary end view, respectively, illustrating a modified locking mechanism for use with the multifunctional tissue dissecting instrument according to the present invention.

DESCRIPTION OF THE PREFERRED EMBODIMENTS

Figure 29:
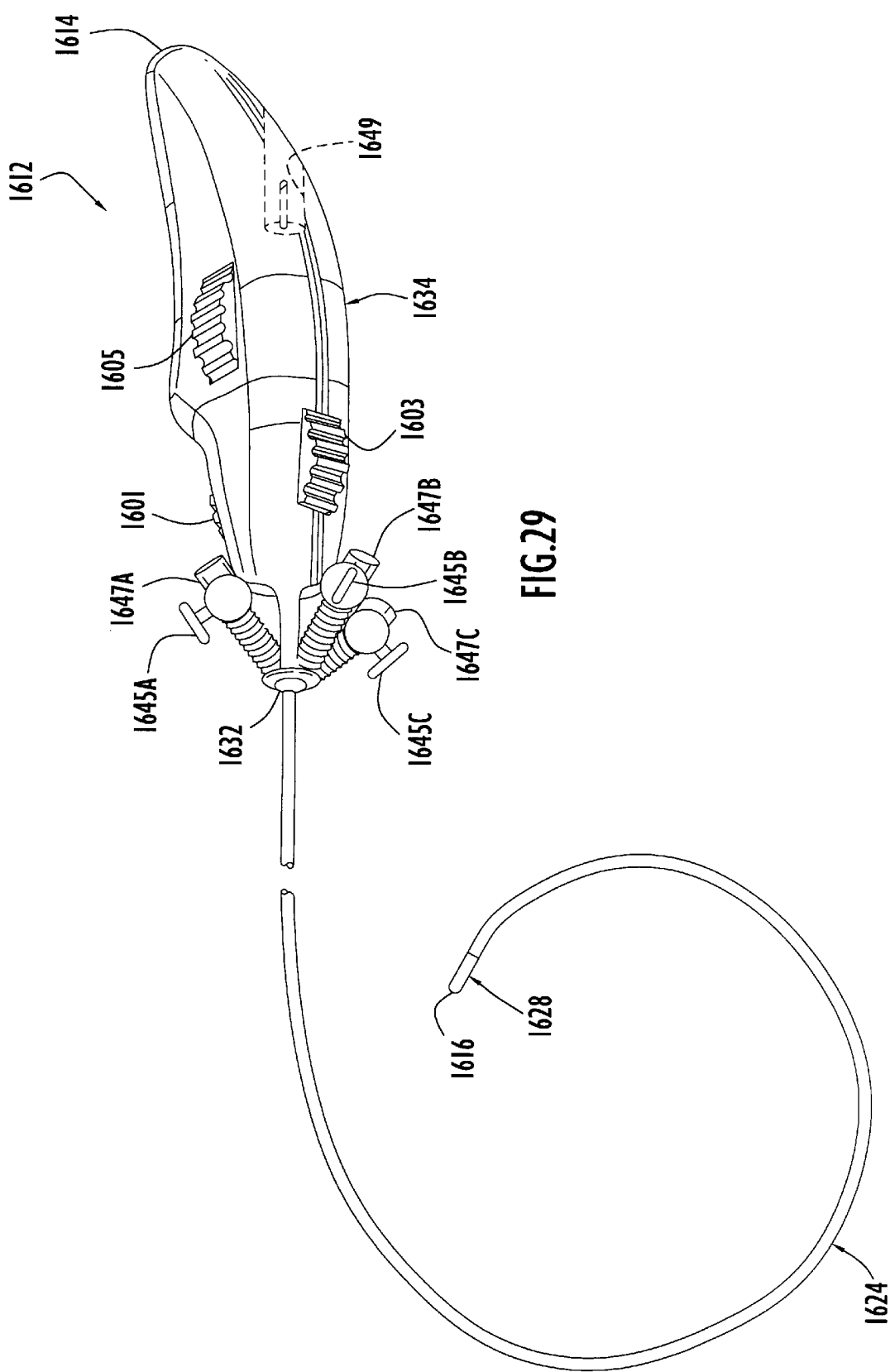
FIG. 29 is a perspective view of a modified blunt dissector according to the present invention.

A multifunctional tissue dissecting instrument 10 according to the present invention, as illustrated in FIGS. 1–6, includes a blunt dissector 12 having a proximal end 14 and a distal end 16, a probe 18 disposed in the blunt dissector and having a tip 20, and a handle 22 coupled with the probe at the proximal end of the blunt dissector and selectively operable to move the probe tip between a retracted position where the probe tip is disposed within the blunt dissector and an extended position where the probe tip protrudes from the distal end of the blunt dissector. Blunt dissector 12 includes an outer tubular member 24, an inner tubular member 26 disposed within the outer tubular member and a dissector body 28 disposed around the inner tubular member at a distal end of the outer tubular member. Outer tubular member 24 is shown having a hollow, cylindrical configuration and includes a distal end 30 and a proximal end 32 secured to a hub 34. It will be appreciated, however, that the outer tubular member can have any configuration to fit through an endoscopic portal into an anatomical cavity. As best seen in FIGS. 2 and 3, inner tubular member 26 is disposed concentrically within outer tubular member 24 in spaced relation thereto to define a radial space or gap therebetween along the length of the outer tubular member. A pair of longitudinal walls or partitions 36a and 36b extend radially outward from diametrically opposed sides of inner tubular member 26 to connect with an inner surface of tubular member 24 thereby dividing the radial space between the inner tubular member and the outer tubular member into a pair of parallel operating channels or passages 38a and 38b of arcuate configuration in transverse cross-section along the entire length of the outer tubular member. Inner tubular member 26 includes a proximal end 40 secured to hub 34 and a distal end 42 which protrudes distally beyond distal end 30 of tubular member 24 to serve as a spine or mandrel about which the dissector body 28 is mounted or formed. Inner and outer tubular members can be formed of any suitable, medically acceptable material, such as plastic or stainless steel, and can be made rigid, semi-rigid or flexible. While the inner tubular member and partitions are shown as being integrally formed with the outer tubular member, it will be appreciated that the inner tubular member and partitions can be formed separately of the outer tubular member and each other using the same, similar or different materials and, further, that the portion of the inner tubular member protruding beyond the distal end of the tubular member can be formed separately of the proximal portion of the inner tubular member and/or made of a different material, e.g., to facilitate detachment of the dissector body from the instrument for purposes of sterilization or replacement.

Hub 34 includes a generally solid cylindrical forward section 35 of slightly greater diameter than outer tubular member 24, a first generally solid frustoconical intermediate section 37 proximally joined with the forward section and of increasing cross-sectional size in a proximal direction, a second generally solid frustoconical intermediate section 39 proximally joined with the first frustoconical section and of decreasing cross-sectional size in a proximal direction, and a hollow cylindrical rearward section 41 proximally joined with the second frustoconical section and terminating at proximal end 14 of the blunt dissector. Forward section 35 of the hub mounts respective proximal ends of the outer tubular member and the inner tubular member, and passages 43a and 43b are formed through the cylindrical forward section of the hub at an acute angle relative to the proximal direction of the instrument to communicate operating channels 38a and 38b with valves, for example stop cock valves 45a and 45b, respectively, having couplings 47a and 47b adapted to communicate with a source of suction or a source of irrigating fluid or medicaments for supply to the operative site. As best seen in FIG. 2, a lumen 49 is formed through hub 34 in axial alignment with lumen 50 of inner tubular member 26 to establish a central or main operating channel through the instrument for introducing probes at the operative site as well as for performing irrigation and aspiration and administering medicaments. It will also be appreciated that flexible instruments such as probes can be inserted through passages 43a and 43b and channels 38a and 38b, if desired.

Body 28 can be formed of any suitable material and have any configuration to non-traumatically contact anatomical tissue for blunt dissection, but is preferably formed of an absorbent and expandable material having, in a dry unexpanded state, a proximal portion 44 of hollow, substantially cylindrical configuration and a rounded distal portion 46 of substantially hemispherical configuration. The dissector body described hereinafter is formed of an absorbent body of material mounted at the distal end of outer tubular member 24 around the protruding distal portion of inner tubular member 26 and extending distally beyond the inner tubular member to cover the distal end of the inner tubular member along an outer peripheral edge thereof. An opening or passage 48 extends longitudinally through rounded distal portion 46 to communicate with lumen 50 of the inner tubular member. The body can, for example, be made of a medical grade material inherently able to absorb or made to absorb body fluids and, preferably, expand substantially from its size in a dry state, the expansion being dependant upon the procedure being performed and the size of the endoscopic portal. The material is preferably relatively rigid or stiff in the dry state to allow introduction to the operative site through the portal; however, some flexibility may be desired dependent upon the configuration of the endoscopic portal and the procedure to be performed. While an expandable material is preferred, if desired, the material can be non-expandable as long as the material is soft and pliant in the wet state. That is, the material should preferably have the characteristics, when wet, of being soft enough to bend freely and repeatedly without breaking and of being malleable and flexible. Sponge materials are believed to be the most effective for the absorbent body of the instrument. Examples of materials which can be used include compressed cellulose sponge, natural sponge, synthetic sponge made of a reaction product of polyvinylalcohol and formaldehyde, hydrophilic cross-linked polyurethane foam as disclosed in U.S. Pat. Nos. 3,369,544 to Crockford, 3,903,232 to Wood et al, 4,098,728 to Rosenblatt and 4,553,966 to Korteweg, and compacted gauze or cotton. Normally no-absorbent materials such as silicone rubber and latex rubber can be made to absorb body fluids, for example by creating passages therethrough in communication with a source of suction, and can thus also be used to form an absorbent dissector body. In the dry state, the absorbent body must be sufficiently rigid to allow the instrument to be used to contact and move or position tissue to facilitate dissection of the tissue. In the dry state, therefore, the blunt dissector is essentially a sponge stick. The outer diameter or cross-sectional size of absorbent body 28 in the dry state will depend upon the size of the portal through which the instrument is introduced as well as the procedure to be performed but will typically range from about 1 mm to about 10 mm in diameter.

The construction of absorbent body 28 is dependent upon the type of material employed and the procedure to be performed including the force required to remove the device after the procedure is completed. To this end, inner tubular member 26 can pass centrally through the body, as shown, to form a core-like support or spine attached to the material along the length thereof or can extend through or along the body at any position, or the body can have one or more spines disposed therein. Referring to FIGS. 2 and 6, in particular, a plurality of spines 52 are shown disposed longitudinally in body 28 at angularly spaced locations about the periphery of the inner tubular member, each spine being formed of a tubular member or trunk 54 with branches 56 extending therefrom at an acute angle to the distal direction with the branches being flexibly or movably mounted to allow the branches to be compressed in substantial alignment with the trunk when the absorbent body of material is in a dry state and compressed around the inner tubular member and spines, and to allow the branches to move outwardly toward predetermined extended positions when the body is in the wet state, for example to cause the body to assume a predetermined shape such as the round or spherical shape shown in FIG. 6. The spines 52 can be provided with or without branches and can either be tubular or solid or the branches 56 can be solid with only the trunk 54 being tubular. Additionally, each spine can have a normal, non-straight configuration, such that when the body is in a wet state it will assume a predetermined, non-straight configuration. Referring to the spines shown in FIG. 6, each trunk 54 is tubular and straight with an open proximal end 58 communicating with one of channels 38a and 38b and an open distal end 60 defining an aperture or opening in the exterior surface of absorbent body 28. Lateral holes or perforations 61 are preferably formed at spaced locations in each trunk to allow selective or continuous irrigation and aspiration via the absorbent body, spines and one or both of the channels as well as drainage of body fluids from the absorbent body when it is wet, for example prior to withdrawal of the tissue dissecting instrument. Additionally, medicaments or other therapeutic substances can be introduced to the operative site via the couplings, spines and absorbent body.

Spines 52 can be formed of a suitable material such as string, plastic or metal. In accordance with one aspect of the present invention, each spine has resilient, spring-like properties and has a normal state, condition or configuration wherein trunk 54 is straight and branches 56 extend outwardly of trunk 54 at an acute angle relative to the distal direction. For purposes of illustration, the branches are shown with varying lengths such that terminal ends of the branches are arranged along a curved path or arc. While the trunk and branches of each spine are shown as being straight in the normal condition, it will be appreciated that spine 52 and/or branches 56 can have various simple or complex curved or partially straight shapes in the normal condition. To this end, the spine can be made of spring metal to have a predetermined normal condition wherein the branches extend laterally outward from the trunk and/or the branches and trunk have a predetermined, non-straight configuration; and, when the instrument is manufactured, the spine is straightened and the absorbent material 28 is attached to the spine, for example with adhesive, such that the dry, stiff condition of the material 28 maintains the spine in a substantially straight configuration with branches 56 folded against trunk 54 as shown in FIG. 2. Accordingly, instrument 10 can be inserted through a portal when the absorbent body of material 28 is dry; and, once the instrument is in the body, material 28 will absorb body fluids to become soft and allow the spine to return to its normal configuration producing a predetermined configuration for use in specific procedures. While it is preferred for the spines to have shape memory, it is also acceptable to use spines with or without branches to reinforce the absorbent body and/or to provide fluid communication with the absorbent body. The absorbent body can also be made of a material having shape memory characteristics, if desired.

Handle 22 is disposed at the proximal end of blunt dissector 12 and includes a first handle member 62 of frustoconical configuration proximally joining the hub and increasing in cross-sectional size in the proximal direction, a second handle member 64 of disc-like configuration proximally spaced from the first handle member and mounting probe 18, and an optional U-shaped handle extension or grip 66 extending between the first and second handle members. Handle member 62 is also shown carrying a hollow, cylindrical extension 68 configured to mate with the hollow, rearward section 41 of hub 34 in a detachable manner, for example by threadedly engaging the hub as shown, by coupling frictionally with the hub or by any other suitable method of attachment. The optional U-shaped grip 66 includes a pair of spaced, parallel legs 70a and 70b extending downwardly, looking at FIGS. 1 and 2, from probe 18 and the first handle member 62, respectively, to connect with an upwardly curved arcuate portion 72. The handle components can be formed separately or as a one-piece unit of any suitable, medically acceptable material such as, for example, plastic; in either case, it is preferred that the U-shaped portion of the handle be of onepiece, spring material construction as shown or bifurcated centrally as shown in phantom at 73 in FIGS. 1 and 2, and provided with a leaf spring 75 or the like so that the legs of the U-shaped handle extension are normally urged apart.

As best seen in FIG. 2, probe 18 includes proximal and distal portions 74 and 76 of generally tubular configuration.

Proximal probe portion 74 is fixedly secured to the second handle member 64 and extends therefrom in a distal direction through an opening in the first handle member 62 to terminate at an outwardly extending flange 77 slidably disposed in hollow cylindrical extension 68. Distal probe portion 76 is adapted to couple with proximal probe portion 74, for example by threadedly engaging an internally threaded recess formed in flange 77, and extends therefrom to terminate distally at tip 20. A bias member 78 is connected between flange 77 and cylindrical extension 68 to bias the probe proximally relative to the cylindrical extension and, when the cylindrical extension is coupled with the hub, relative to blunt dissector 12. As shown, bias member 78 includes a helical coil spring disposed around probe 18 and mounted in compression between flange 77 and a distal wall of the cylindrical extension to bias the probe proximally toward a retracted or protected position where the flange abuts the first handle member 62 and probe tip 20 is proximally spaced from the distal end of blunt dissector 12. It will be appreciated, however, that bias member 78 can include various other types of springs as well as other types of bias devices including compression springs, tension springs, torsion springs, pan springs, leaf springs, rubber, plastic or magnets, for example. Proximal probe portion 74 is preferably formed of an electrically insulative plastic material, but can be formed of any suitable material so long as any exposed parts of the probe are insulated. An electrical connector 79 is disposed proximally of the second handle member 64 on proximal probe portion 74 and is connected with distal probe portion 76, which is preferably formed of an electrically conductive material for performing unipolar or bipolar electric coagulation and cautery, for example. Proximal probe portion 74 also carries a valve 80 with a coupling 81 adapted to communicate with a source of suction or a source of irrigating fluid, and the valve and coupling are disposed proximally of the electrical connector.

A locking mechanism 82 allows probe 18 to be manually locked in any position relative to hub 34 and includes a push-button 83 mounted on the first handle member 62 in radial relation to the probe and a plurality of longitudinally spaced teeth 84 carried or formed on the probe in opposed relation to the button. Teeth 84 include distal surfaces inclined at an acute angle relative to the proximal direction and proximal surfaces oriented substantially perpendicular or transverse to the instrument longitudinal axis, and a lower end of button 83 is beveled at an acute angle relative to the proximal direction to form a latch which mates with teeth 84 so that, when the button is depressed as shown in FIGS. 1 and 2, the latch will be lowered or moved downwardly, looking at FIG. 2, from a normally unlocked position above the teeth to a locked position adjacent the teeth in order to prevent proximal movement of the probe relative to the hub. When the button is depressed again, the latch is lifted upwardly, looking at FIG. 2, from the locked position shown by solid lines to the unlocked position shown by broken lines in order to allow the probe to move relative to the hub. The latch can also be configured to allow a ratcheting-type movement of the probe whereby the probe is able to move distally when the latch is in the depressed condition but is prevented from moving proximally when the handle is released.

The multifunctional tissue dissecting instrument can be provided with parts assembled as shown in FIGS. 1 and 2 or in a disassembled state wherein parts of the multifunctional tissue dissecting instrument are provided separately and assembled by the user. If provided in a disassembled state, assembly of the parts discussed so far involves choosing an appropriate blunt dissector and probe based upon the type of anatomical tissue to be dissected and the procedure to be performed and coupling the probe with the blunt dissector using a handle so that the probe can be moved relative to the blunt dissector.

In use, multifunctional tissue dissecting instrument 10 will normally be inserted through a portal sleeve or cannula in the condition shown in FIGS. 1 and 2 with absorbent body 28 in a dry, unexpanded state and probe tip 20 in a retracted or protected position disposed proximally of inner tubular member distal end 42. Absorbent body 28 at the distal end of the blunt dissector can then be used to dissect, retract or otherwise manipulate anatomical tissue in the body by grasping hub 34 or handle 22 and manipulating the instrument to cause the absorbent body of material to contact the anatomical tissue. Absorbent body 28 can also be used to absorb body fluids, whereupon the body of absorbent material will preferably expand and become soft and flexible so that spines 54 can assume their predetermined configurations as shown in FIG. 6. Couplings 47a and 47b can also be communicated with a source of suction to drain fluid from the body of absorbent material or with a source of irrigating fluid for supplying fluid to the operative site via the body of absorbent material or, if desired, one of the couplings can be communicated with a source of suction and the other coupling can be connected with a source of irrigating fluid, etc.

Probe tip 20 is moved from the protected position within the inner tubular member of blunt dissector 12 to an extended position protruding distally from the inner tubular member, as shown by broken lines in FIG. 2, to dissect certain types of anatomical tissue which are not easily dissected using the blunt dissector and to perform other functions at the operative site such as, for example, cutting, coagulating, cauterizing, irrigating, aspirating and administering medicaments. Referring still to FIG. 2, it can be seen that a squeezing action on legs 70a and 70b of handle grip 66 causes probe 18 to move distally relative to hub 34 against the proximal bias of bias member 78 thereby moving probe tip 20 from the retracted position shown by solid lines in FIG. 2 to the extended position shown by broken lines in FIG. 2. In the extended position, probe tip 20 is exposed and can be used to puncture anatomical tissue; and, if connected to a source of electrical energy, the probe tip can be used as an electrocautery for unipolar or bipolar electrosurgery to cut, coagulate and cauterize tissue for dissection. When the probe tip is no longer needed, the squeezing pressure on legs 70a and 70b is relieved, allowing bias member 78 and/or the resilience of U-shaped handle extension 66 to move the probe proximally relative to the blunt dissector so that probe tip 20 moves to the protected non-exposed or retracted position within the blunt dissector. For procedures where the probe tip must be extended for prolonged periods of use, locking mechanism 82 can be employed to hold the probe tip at any extended position by depressing button 83 to lower the latch between teeth 84 on the probe. When use of the probe is no longer needed or desired, the locking mechanism can be disengaged by pressing on the button a second time to lift the latch away from the teeth and by relieving pressure on legs 70a and 70b of the handle extension or grip. When the legs of the handle grip are released, probe 18 is moved proximally relative to hub 34 under the influence of bias member 78 and the resilience of grip 66 causing probe tip 20 to be moved proximally from the extended position to the retracted position so that the instrument can then be used as a blunt dissector.

Probe 18 is preferably hollow as shown in FIGS. 2 and 6 to define a central operating passage or channel through the instrument to permit passage of additional instruments and fluids therethrough, or the probe can be solid as shown in FIG. 7 at 118. In either case, an electrically insulative layer, shown by broken lines at 185 in FIG. 7, can be formed along the length of the probe, if desired, for an added measure of security or when conductive materials are used in constructing portions of the blunt dissector that may contact the probe.

While sharp, needle-like probe tips are shown in FIGS. 6 and 7, it will be appreciated that the tip of the probe can have any configuration useful for performing an endoscopic procedure. For example, in FIGS. 8 and 9, a modification of a tissue dissecting instrument according to the present invention is shown wherein the modified tissue dissecting instrument 210 includes a probe 218 having a generally L-shaped tip 220 and a blunt dissector 212 having a pocket or recess 289 formed therein at a distal end to receive the L-shaped probe tip when the probe tip is retracted. Probe tip 220 includes a leg 286 which extends perpendicularly from a bend 287 at the distal end of the probe and terminates at a beveled end 288 acutely angled relative to the distal direction. In the retracted position, shown by solid lines in FIG. 8, probe tip 220 is received within recess 289 and is in a protected, non-exposed condition or state allowing the instrument to be used as a blunt dissector. When additional capabilities or functions are needed or desired, the L-shaped probe tip can be moved from the retracted position to an extended position, shown by broken lines in FIG. 8, for example to engage anatomical tissue in a hook-like manner so that the tissue can be manipulated or pulled.

In FIGS. 10 and 11, another modification of a tissue dissecting instrument according to the present invention is shown wherein the modified tissue dissecting instrument 310 includes a probe 318 having a generally J-shaped tip 320 and a blunt dissector 312 having a pocket or recess 389 formed therein at a distal end to receive the J-shaped probe tip when the probe tip is retracted. Probe tip 320 includes a leg 386 extending substantially parallel to a longitudinal axis of the probe from a 180° bend 387 at a distal end of the probe to terminate at a beveled end 388 acutely angled relative to the proximal direction. The radius of curvature of the bend is such that, when the probe tip is retracted, the probe tip will be disposed in the recess in a non-exposed, protected state or condition as shown by solid lines in FIG. 10. In the extended position, shown by broken lines in FIG. 10, probe tip 320 will be exposed and the instrument can, for example, be used in a hook-like manner to manipulate and pull anatomical tissue.

A further modification of a tissue dissecting instrument according to the present invention is illustrated in FIGS. 12 and 13 wherein the modified instrument 410 includes a probe 418 having a tip 420 with a pair of opposed scissor blades 490 resiliently biased apart at the distal end of the probe and a blunt dissector 412 having a pair of slit-like recesses 489 formed at a distal end on opposite sides of inner tubular member 426 in diametrically opposed relation to receive and stabilize the blades of the probe tip as the probe tip is moved between retracted and extended positions. The blades move apart resiliently to be angularly spaced from one another when the probe tip is extended, as shown by broken lines in FIG. 12, and close against one another to cut anatomical tissue and/or other materials disposed between cutting edges of the blades as the probe tip is retracted, as shown by solid lines in FIG. 12. Alternatively, probe 418 can include or be telescopically received within a tubular member or sleeve (FIG. 26) which is movable relative to the probe tip in order to operate the blades.

In FIGS. 8, 10 and 12, the absorbent bodies are shown without branched spines for purposes of clarity; it will be appreciated, however, that the absorbent body can be formed with or without tubular members or spines therein dependent upon the material from which the body is constructed and the type of tissue to be dissected. In FIG. 14, a modified tissue dissecting instrument 510 according to the present invention is shown having a segmented inner tubular member 526 formed of a proximal portion or segment 591 disposed in outer tubular member 524 and a distal portion or segment 592 protruding distally from the outer tubular member through absorbent body 528. Distal segment 592 is detachably coupled with proximal segment 591, for example by friction fit, to facilitate sterilization or disposal, and is preferably formed of a flexible material to allow the absorbent body 528 to bend under the pressure of tissue contact, if desired, as shown by broken lines in FIG. 14. It will be appreciated, however, that distal segment 592 of the inner tubular member can be detachably coupled or fixedly secured to the proximal segment and can be formed of a rigid, semi-rigid or flexible material as desired. When formed of a flexible or resilient material such as, for example, rubber, the inner tubular member can have a normally closed configuration as shown in FIGS. 14A and 14B at 526' wherein the lumen 550' of the inner tubular member is partly or completely closed and is capable of stretching or expanding to accommodate instruments of various sizes inserted through the inner tubular member.

The tissue dissecting instrument can also be formed without an inner tubular member or spines as shown in FIG. 15 at 610, in which case a passage or channel 693 is preferably formed through the absorbent body of material 628 in longitudinal alignment with the probe tip 620 to permit extension and retraction of the probe tip therethrough in a manner similar to that described above. The probe 618 can also be modified to have a main body portion 694 of greater cross-sectional size or diameter than the probe tip 620 in order to increase the pressure at the tip of the probe when fluids are passed therethrough. FIG. 15 also shows another method of attaching the absorbent body 628 to the outer tubular member 624 wherein a step or shoulder 695 is formed along an outer peripheral edge of the outer tubular member at the distal end thereof and the absorbent member is provided with a peripheral rim 696 configured to fit over the step or shoulder and be held in place by adhesive bonding, friction fit or any other suitable form of attachment.

As mentioned previously, the absorbent body of the blunt dissector can be constructed to have any useful configuration in an expanded or unexpanded state. In FIG. 16, for example, a modified absorbent body 728 for use with the tissue dissecting instrument according to the present invention is shown wherein the modified absorbent body has an ovoid configuration in an expanded state with a major axis aligned with the longitudinal axis of the tissue dissecting instrument. In FIG. 17, a similar modified absorbent member 828 is shown having an ovoid configuration in an expanded state with the major axis oriented at an acute angle relative to the longitudinal axis of the instrument. In the latter case, the probe 818 is preferably flexible to permit movement of the probe through the absorbent body in the expanded state as shown by broken lines in FIG. 17. Another modification of an absorbent body for use with the tissue dissecting instrument according to the present invention is shown in FIG. 18 at 928. The modified absorbent body 928 includes a spine 952 having a plurality of angularly extending branches 956 in an expanded state to define a generally triangular configuration particularly useful for organ manipulation and uterine manipulation.

The outer or external surface of the absorbent body at the distal end of the blunt dissector can be solid or porous and smooth or rough depending upon the material from which the absorbent body is constructed as well as the tissue to be dissected. For example, in FIG. 19 a modified absorbent body 1028 is shown having spines 1052 with longitudinally extending trunks 1054 and branches 1056 extending angularly therefrom to elevate portions of the absorbent body in order to create an irregular or rough exterior surface.

In FIG. 20, a detachable absorbent body 1128 for use with the tissue dissecting instrument according to the present invention is shown having a coupling 1197 at its proximal end which is externally threaded to couple with an internally threaded portion 1198 at the distal end of outer tubular member 1124. Distal end 1142 of inner tubular member 1126 is proximally spaced from distal end 1130 of the outer tubular member and is axially aligned with a tubular segment 1192 disposed in the absorbent body to be telescopically received therein when the absorbent body is coupled with the outer tubular member to assemble the blunt dissector. While a threaded coupling is shown for attaching the absorbent body to the outer tubular member, it will be appreciated that the absorbent body can be attached to one or both of the inner and outer tubular members and that other forms of attachment can be used including, but not limited to, friction fittings, detents, and Luer fittings. Furthermore, it will be appreciated that the absorbent body can have any of the configurations previously described or any other configuration useful in an endoscopic procedure.

A modified tissue dissecting instrument 1210 according to the present invention, as illustrated in FIG. 21, includes a probe 1218 mounted by a handle 1222 and a blunt dissector 1212 mounted by a hub 1234. The modified handle 1222 includes a housing 1223 having front and rear walls 1225 and 1227, a top wall 1229 and a bottom wall 1231 from which a handle extension 1266 in the form of a pistol grip extends at an angle towards the proximal end of the instrument. Probe 1218 extends through the opening in the front wall of the housing and protrudes proximally through an opening in the rear wall of the housing to connect with a valve 1280 having a coupling 1281. Proximal portion 1274 of the probe is formed of an electrically insulative material or is coated with an electrically insulative material and coupled with distal portion 1276 of the probe in any suitable manner such as, for example, friction fit, adhesive bonding or threaded engagement. The distal portion of the probe is electrically coupled with a connector 1279 via a conductive leaf spring 1299 having a base portion 1201 secured to an exterior surface of the probe distal portion within the housing and extending longitudinally to a bend joining the base with an upwardly angled or transverse portion 1202 extending transversely from the probe toward the top wall of the housing to a second bend joining the transverse portion with a parallel portion 1203 in sliding contact with connector 1279. Handle 1222 includes a trigger 1204 pivotally mounted on a pin 1205 secured to a wall or walls of the housing and including an external trigger portion 1206 having a curvature away from pistol grip 1266 and an inner trigger portion 1207 having a curvature to contact a rear face of flange 1277 on the probe. A bias member 1278, shown as a spring, is disposed around the probe and held in compression between flange 1277 and front wall 1225 of the housing to bias the probe in a proximal direction relative to the handle housing. Locking mechanism 1282 is similar to the locking mechanism shown in FIG. 2 but with the pushbutton mounted at an angle relative to the probe in the back wall 1227 of the handle housing. Handle 1222 is shown in FIG. 21 coupled with hub 1234 but can be adapted to couple with any type of blunt dissector having any type of hub or no hub at all.

The hub 1234 shown in FIG. 21 is of generally hollow, cylindrical configuration with front and rear walls 1235 and 1214. Outer tubular member 1224 extends through an opening in the hub front wall and terminates proximally at a flange 1232 which is rotatably disposed in a recess 1233 formed in the hub front wall. The outer tubular member carries an outwardly extending collar 1221 adjacent the hub which can be grasped by the surgeon and used to rotate the outer tubular member, if desired.

In use, probe 1218 will normally be in a retracted position as shown in FIG. 21 and can be moved distally relative to handle housing 1223 by grasping pistol grip 1266 and pulling on external trigger portion 1206 to cause the trigger to rotate in a counterclockwise direction, looking at FIG. 21, so that internal trigger portion 1207 pushes against flange 1277 to urge the probe distally against the proximal bias of bias member 1278. When the trigger is released, the probe will return to the retracted position under the influence of the bias member or, if it is desired for the probe to be held in an extended position, pushbutton 1283 of the locking mechanism can be depressed to cause the latch at the distal end thereof to engage teeth 1284 at the proximal end of the probe as shown by broken lines in FIG. 21.

Another modification of a tissue dissecting instrument according to the present invention is shown in FIG. 22 at 1310 and includes a probe 1318 mounted by a handle 1322 having a U-shaped handle extension or grip 1366 similar to handle grip 66, and a blunt dissector 1312 having a hub 1334 similar to hub 1234 but with valve passages 1343a and 1343b extending downwardly from the hub, looking at FIG. 22, alongside distal leg 1370b of the handle extension 1366 when the handle is coupled with the hub. Probe flange 1377 is mounted by a handle housing 1323 attached to proximal leg 1370a of the handle grip and movable relative to the hub when the handle is coupled therewith. Housing 1323 is of generally cylindrical configuration with a rearwall 1327 having a recess therein receiving the probe flange 1377 and an inwardly extending flange 1325 at a distal end of the cylindrical wall of the housing. Handle housing 1323 includes a distal extension 1368 of hollow, cylindrical configuration which extends into the housing and terminates in an outwardly extending flange 1369. A distal end of the cylindrical extension is configured to mate with the hub when the probe is inserted through the blunt dissector and distal leg 1370b of the handle extension abuts valve passages 1343a and 1343b. A bias member 1378 is held in compression between a proximal end of the handle housing and the distal end of the cylindrical extension to bias the probe proximally relative to the hub to a retracted position where inwardly extending flange 1325 of the housing abuts outwardly extending flange 1369 of the cylindrical extension thereof. A modified locking mechanism 1388 is also shown in FIG. 22 and includes a transverse wall or flange 1309 extending upwardly from the handle housing, looking a FIG. 22, and a lever 1383 pivotally mounted on a pin 1308 secured to the upwardly extending wall. A lower end of lever 1383 is tapered or beveled at an acute angle relative to the distal direction and angled teeth 1384 are formed or carried on the cylindrical extension of the handle housing in opposed relation to the lever so that when the lever is in an upright position as shown by solid lines in FIGS. 22 and 23, the beveled lower end of the lever will engage the teeth and prevent proximal movement of the housing relative to the extension (and the hub when the handle is coupled with the blunt dissector as shown). The handle housing can be released by rotating the lever clockwise or counterclockwise, as shown by broken lines in FIG. 23, whereupon the lower end of the lever is angularly displaced relative to the teeth allowing the teeth to pass through a slot or groove in housing flange 1325 without obstruction. It will be appreciated that valve passages 1345*a* and 1345*b* can extend at any angle relative to a longitudinal axis of the instrument and in any direction to communicate with a source of suction, a fluid source or instruments to be inserted through the passages. For example, the valve passages can extend upwardly relative to the handle housing, as shown by broken lines in FIG. 22.

Another modification of a tissue dissecting instrument according to the present invention is shown in FIG. 24 at 1410 and includes a hub 1434 at the proximal end of a blunt dissector 1412, a probe 1418, and a modified handle 1422 similar to handle 22 but without a U-shaped handle extension and having a tubular probe carrier or sleeve 1451 for coupling with and carrying the probe. Probe carrier 1451 is fixedly secured to second handle member 1464 and extends therefrom in a distal direction through an opening in first handle member 1462 to terminate at a distal end 1453 disposed in the hub. The probe carrier includes an outwardly extending flange 1477 slidably disposed in the hollow cylindrical portion 1441 of the hub and extends proximally through the second handle member to terminate at a valve 1455 with a coupling 1457 which can, for example, be internally threaded as shown to mate with a coupling 1459 on probe 1418 such that the probe can be attached to the carrier and moved therewith by operation of handle 1422. Probe 1418 is shown as a hollow needle having an externally threaded coupling 1459 to mate with coupling 1457 at the proximal end of the probe carrier and a female coupling 1481 at a proximal end to communicate with a source of suction, a fluid source or other instruments. A valve 1480, such as a stopcock valve, is disposed between the couplings to control passage of fluids and/or instruments through the lumen of the needle. An electrical connector, shown by broken lines at 1479 in FIG. 24, can optionally be mounted at the proximal end of the probe to utilize the probe for electrosurgical procedures, if desired, and the probe can be provided with an electrically insulative layer (shown by broken lines at 1485) to provide an added measure of security or when it is anticipated that the probe may contact conductive portions of the blunt dissector.

Any type of probe can be configured to couple with the probe carrier shown in FIG. 24. For example, in FIG. 25, a probe 1418' in the form of a solid needle is shown having an externally threaded coupling 1459' and an electrical connector 1479' coaxially aligned with a longitudinal axis of the needle. Another probe which can be used with the handle of FIG. 24 is shown in FIG. 26 at 1418" and includes a central member 1463" terminating distally in a pair of scissor blades 1490" resiliently biased apart, an outer member 1465" telescopically receiving the central member and a U-shaped handle 1467" coupling the central member with the outer member to allow movement of the outer member over the blades to cause the blades to close together. With the blades in the closed condition, the modified probe 1418" can be inserted into the probe carrier of handle 1422 and coupled therewith for movement relative to hub 1434 and, thus, the blunt dissector. When the probe tip 1420" is extended, the U-shaped handle can be operated to open and close the scissor-like probe tip as desired.

FIGS. 27 and 28 illustrate a modification of a locking mechanism for use with the tissue dissecting instrument according to the present invention wherein the modified locking mechanism 1582 includes a pair of spaced, parallel flanges or extensions 1570*a* and 1570*b* and a latch 1511 extending transversely through openings formed in the flanges. Flanges 1570*a* and 1570*b* extend outwardly from parts of the instrument that move relative to one another such as, for example, movable parts of the handle; and, it will be appreciated, that if a U-shaped member is connected between the flanges as shown by broken lines at 1566 in FIG. 27, an auxiliary handle extension or grip can be formed. Latch 1511 is an elongate bar that extends from a bulbous enlarged proximal end 1513 disposed proximally of flange 1570*b* to a transversely extending arm 1515 disposed substantially parallel to and distally of flange 1570*a* and terminating at a knob or button 1517. The latch is provided with teeth 1584 on one side thereof and is rotatable within the flange openings to move the teeth between a locked position where the teeth engage a peripheral edge of the opening in distal flange 1570*a* to prevent proximal movement of flange 1570*b* relative to flange 1570*a* and an unlocked position where the teeth do not engage a peripheral edge of the opening in the distal flange and are able to pass through the opening unobstructed thereby allowing proximal and distal movement of the proximal flange relative to the distal flange. The latch can be rotated by moving knob 1517 at the end of arm 1515 as shown in FIG. 28 in a clockwise or counterclockwise direction relative to a longitudinal axis of the latch dependent upon whether the instrument is being operated right handedly or left handedly as well as upon the preference of the user.

The elongate tubular portion of the blunt dissector can be rigid or flexible and can have any suitable cross-sectional size or length dependent upon procedural use. For example, in FIG. 29, a modified blunt dissector 1612 according to the present invention is shown having a flexible outer tubular member 1624 similar in cross-sectional size and length to a conventional catheter but with a dissector body 1628 at the distal end particularly useful in vascular procedures such as, for example, embolectomy procedures. Proximal end 1632 of the outer tubular member is mounted by a hub 1634 having a configuration to be held outside the body. The hub includes valves 1645*a*, 1645*b* and 1645*c* with couplings 1647*a*, 1647*b* and 1647*c* acutely angled relative to the proximal direction and manually-operable guidance controls or knobs 1601, 1603 and 1605 coupled with conventional guidance mechanisms for controlling deflection at the distal end 1616 of the dissector. A lumen or channel 1649 is formed through hub 1634 along a longitudinal axis thereof and in axial alignment with a lumen or channel in the outer tubular member to define a central or main operating channel through the dissector for introducing flexible probes at the operative site as well as for performing irrigation and aspiration and administering medicaments.

In use, the modified dissector 1612 is introduced into a vessel like a conventional catheter and is advanced to the operative site therein by use of guidance controls 1601, 1603 and 1605 and/or by sliding the dissector along a conventional guide wire extending through the main operating channel of the dissector. In the case of an embolectomy, dissector body 28 is preferably an absorbent body of material with sufficient rigidity, when wet, to move an embolism from a site within a blood vessel to the entry site or portal for removal therefrom. The absorbent body can also be used to precisely administer medicaments to specific sites within the vessel.

From the above, it will be appreciated that multiple functions can be performed with a multifunctional tissue dissecting instrument according to the present invention having a probe disposed within a blunt dissector and a handle operable to move a tip of the probe between a retracted or protected position within the blunt dissector and an extended or exposed position protruding from the blunt dissector. With the probe tip in the retracted or protected position, the instrument can be used as a blunt dissector to separate, divide or dissect anatomical tissue along natural or created lines, to perform lysis of adhesion (separation of adhered tissue), to create spaces within the body, to retract and manipulate tissue, to supply fluid for irrigation and suction for aspiration, to administer medicaments, to absorb body fluids and cleanse the operative site as well as to perform other functions dependant upon the configuration of the instrument. With the probe tip in the extended or exposed position, the instrument can be used to manipulate or grasp anatomical tissue, to perform sharp dissection wherein tissue is cut or penetrated to create lines for dissection, to transmit energy such as, for example, electromagnetic, ultrasonic, thermal, electrical or light energy, to perform fluid dissection or to otherwise treat the tissue. In addition, a hollow probe can be used to define an operating channel through the multifunctional instrument for introducing additional instruments or probes, supplying fluids, creating suction and/or administering medicaments at the operative site without withdrawing the multifunctional tissue dissecting instrument from the body.

When used for embolectomy procedures as well as other vascular procedures, the instrument has the advantages over balloon instruments of providing increased rigidity due to spines in the absorbent body to hold the embolism as the embolism is moved to the entry site or portal for removal thereby minimizing the opportunity for the embolism to slip from the instrument, permitting delivery of drugs, such as medicaments and, in particular, anti-coagulants, directly to the wall of the blood vessel through the absorbent member which softly conforms to the surface of the blood vessel to produce increased contact and accurate drug delivery to specific sites and of increased safety by softly engaging the walls of the blood vessel. Dependent upon the procedure to be performed, the spines can be remotely expanded and contracted such that spine deployment can be both active and/or passive. It will also be appreciated that delivery of drugs directly to the walls of the blood vessels obviates the need for blocking or occluding a blood vessel at spaced locations as is commonly done to supply drugs to specific sites, for example in gene therapy. Since the instrument has a central channel passing through the absorbent body, blood flow can be continued with the dissector body in place.

The blunt dissector can be used alone or together with the probe dependent upon the procedure to be performed. While the blunt dissector has been shown as an elongate tubular member with an absorbent body of material at a distal end, it will be appreciated that the blunt dissector can have any configuration to fit through a portal (such as a cannula or an incision) into an anatomical cavity and to contact anatomical tissue and absorb body fluids in the anatomical cavity while defining an operating passage or channel through the anatomical cavity wall for introducing additional instruments or probes, supplying fluids, creating suction and/or administering medicaments. The term "portal" as used herein means any small opening providing access to internal operative sites regardless of whether the opening is formed as a structural channel, such as a sleeve, a cannula or the operating channel of an endoscope, or a narrow incisional or natural entry opening. The blunt dissector can, for example, be configured like a conventional kitner but with one or more operating passages or channels formed therethrough, or the blunt dissector can be formed of a length of absorbent material with one or more passages or channels formed therethrough, or with one or more absorbent bodies of material disposed at various locations along the length of a tubular member.

The dissector body can be made of any type of medical grade material suitable to contact anatomical tissue for blunt dissection but is preferably made of a material that can inherently absorb body fluids or be made to absorb body fluids and, preferably, expand substantially from its size in a dry state, the expansion being dependent upon the procedure being performed and the size of the endoscopic portal. When the dissector body is formed of an absorbent body of material, the material is preferably relatively rigid or stiff in the dry state to allow introduction to the operative site through the portal; however, some flexibility may be desired dependent upon the configuration of the endoscopic portal and the procedure to be performed. While an expandable material is preferred, if desired, the material of the absorbent body can be non-expandable so long as the material becomes soft and pliant in the wet state after absorption of body fluids. That is, the material of the absorbent body should have the characteristics, when wet, of being soft enough to bend freely and repeatedly without breaking and of being malleable and flexible.

The dissector body can have any configuration to non-traumatically contact anatomical tissue for dissection including, but not limited to, configurations utilizing membranes, absorbent and non-absorbent materials, and spines, either alone or in any combination. The softness of the dissector body, measured in terms of hardness or durometer, can vary along the length, width or through the thickness of the body. If provided, spines can be disposed completely within the dissector body or made to protrude therefrom like bristles of a brush. The spines can each have a predetermined shape and can be held in a flattened or compressed condition by an absorbent body of material when the material is dry and can then impart a rigidity or shape to the absorbent body of material when the absorbent body of material is soft and wet. When an inner tubular member is provided within the elongate, outer tubular member, the inner tubular member can extend through the dissector body as a spine or terminate proximally of the dissector body in alignment with a passage formed through the dissector body. If provided, the inner tubular member can be disposed concentrically or eccentrically within the outer tubular member to define one or more operating passages or channels between a proximal end of the blunt dissector and the dissector body. Alternatively, the elongate outer member can be formed of a substantially solid length of material with passages or channels formed therethrough. In this regard, the blunt dissector is preferably formed with a hub at a proximal end defining one or more valve passages therethrough in communication with the passages or channels formed in the outer member. If provided, the hub will preferably have a configuration to be held by the user outside the anatomical cavity and to couple with the handle for operating a probe, if desired. While various hubs are shown having valves extending at an acute angle relative to the proximal direction, it will be appreciated that the valves can be located anywhere on the hub and at any angle relative to the longitudinal axis of the instrument. Furthermore, it will be appreciated that the absorbent body can be formed of a normally non-absorbent material which is made to absorb body fluids, for example by forming a plurality of passages therethrough in communication with a source with suction, and that the absorbent bodies described and shown herein can be covered with a microporous medical fabric or membrane or a balloon, and that balloons or membranes can be imbedded within, under or over the absorbent body, as desired.

In the wet, expanded state, the absorbent body can have any configuration or shape useful for contacting anatomical tissue to be dissected or manipulated, creating space or accessing regions within the body where fluids are to be supplied or suction is to be created. When carried by a tubular member, the absorbent body can be disposed completely or partly around the tubular member and can be fixed thereto or detachable therefrom for sterilization or disposal.

The probe can have any configuration to fit through an operating channel or passage in the blunt dissector and perform additional functions at the operative site when extended from the blunt dissector. For example, the tip of the probe can be configured like a hollow or solid needle with a sharp, tissue penetrating point, like a hook, or like a scissors. Moreover, the probe can be made to protrude axially, laterally or at any angle relative to a longitudinal axis of the instrument. It will also be appreciated that endoscopes can be incorporated into the probes or inserted directly through the blunt dissector to visualize the operative site. The probes are preferably hollow to define or maintain an operating passage or channel through the instrument through which additional instruments and fluids can pass. When a probe includes a tubular body or shaft closed at a distal end and a hollow needle or hook extends from an opening in the closed distal end, the probe can be used to precisely administer medicaments such as vasoconstrictors (e.g. epinephrine) or other fluids to the operative site, or for passing lengths of suture material through the hollow needle or hook to suture tissue within the anatomical cavity.

The probe is preferably biased proximally relative to the blunt dissector, for example within a housing configured to mount the proximal end of the blunt dissector in a releasable manner. When provided, the housing can be formed integrally with the proximal end of the blunt dissector, can be carried by a handle, or the probe can be biased proximally relative to the blunt dissector without a housing, for example using a resilient, U-shaped handle extension as shown in FIGS. 1 and 2.

The handles shown and described herein for moving the probe relative to the blunt dissector are exemplarily of the types of conventional handles suitable for performing the function of extending the tip of a probe; accordingly, the handles can have any configuration for producing relative movement between the probe and the blunt dissector including, but not limited to, axially spaced handle members or finger rests, pivoted legs with finger loops, one fixed and one pivoted leg with finger loops, a pistol grip with a movable trigger, or resilient U-shaped members connected between spaced handle members mounting the blunt dissector and the probe, respectively. Moreover, the handles can have any orientation relative to the longitudinal axis of the instrument including, for example, substantially transverse orientations wherein the handles extend transversely from the instrument longitudinal axis or substantially longitudinal orientations wherein the handles extend longitudinally from a rear of the instrument and are operated like a scissors, or even rotatable configurations wherein the handles can be moved between transverse and longitudinal orientations as desired.

Any locking mechanism including, but not limited to, levers, spring-biased detents or push-buttons, can be used to lock the probe at any location relative to the blunt dissector. The locking mechanism is preferably mounted at the proximal end of the blunt dissector to allow one-handed operation of the instrument but can be mounted anywhere on the instrument.

The blunt dissector, probe and handle can be provided as an integral unit or formed as separate units for assembly by the user. If formed as separate units, the blunt dissector and probe can have any configuration for being releasably coupled including threaded or telescoping portions, detents, latches or any other type of suitable connection.

The components of the multifunctional tissue dissecting instrument of the present invention can be made of any suitable, medical grade materials to permit sterilization for reuse or disposal for single-patient use. The components can be made of multiple parts of various configurations and materials to reduce cost. Furthermore, the blunt dissector, probe and/or handle can have various valves, stop cocks and seals to control fluid flow therethrough.

The features of the various embodiments can be combined in any manner desired dependent upon the operational requirements of the procedure to be performed and the construction of the instrument.

Inasmuch as the present invention is subject to many modifications, variations and changes in detail, it is intended that all subject matter discussed above or shown in the accompanying drawings be interpreted as illustrative only and not be taken in a limiting sense.

What is claimed is:

1. A multifunctional tissue dissecting instrument for use in a surgical procedure of the type where a portal is established to provide access to an operative site within an anatomical cavity and said instrument is introduced to the operative site through the portal, said multifunctional instrument comprising a blunt dissector having a distal end adapted to be introduced into the anatomical cavity through the portal, a proximal end adapted to be positioned externally of the anatomical cavity, and a dissector body disposed at said distal end to contact anatomical tissue for blunt dissection;

a probe disposed within said blunt dissector and having a tip movable between a retracted position where said probe tip is disposed within said blunt dissector and an extended position where said probe tip protrudes from said distal end of said blunt dissector; and a handle disposed at said proximal end of said blunt dissector and coupled with said probe, said handle being selectively operable to move said probe tip between said retracted and extended positions, whereby said instrument can be used as a blunt dissector when said probe tip is moved to said retracted position and said instrument can be used to treat anatomical tissue with said probe when said probe tip is moved to said extended positions;

wherein said blunt dissector includes an elongate tubular member having proximal and distal ends and said dissector body includes an absorbent body of material disposed on said tubular member distal end for contact with tissue and wherein said probe is disposed in said tubular member.

2. A multifunctional tissue dissecting instrument as recited in claim 1 and further comprising bias means for biasing said probe tip toward said retracted position.

3. A multifunctional tissue dissecting instrument as recited in claim 2 and further comprising a locking mechanism selectively operable to prevent movement of said probe tip relative to said blunt dissector.

4. A multifunctional tissue dissecting instrument as recited in claim 3 wherein said locking mechanism includes a push-button that is operable to alternately lock and release the probe.

5. A multifunctional tissue dissecting instrument as recited in claim 1 wherein said absorbent body of material protrudes distally from said distal end of said tubular member and wherein a passage is formed through said absorbent body in alignment with said probe tip to permit said probe tip to pass through said absorbent body when said probe tip is moved between said retracted and extended positions.

6. A multifunctional tissue dissecting instrument as recited in claim 5 and further comprising an inner tubular member extending through said elongate tubular member in spaced relation thereto in order to define a gap therebetween for establishing an operating channel communicating between said absorbent body at a distal end of said elongate tubular member and at least one of a valve and a coupling at a proximal end of said elongate tubular member.

7. A multifunctional tissue dissecting instrument as recited in claim 6 wherein a plurality of operating channels are defined in the gap between said inner tubular member and said elongate tubular member, said operating channels each communicating between said absorbent body and at least one of a valve and a coupling at said proximal end of said elongate tubular member.

8. A multifunctional tissue dissecting instrument as recited in claim 1 wherein said blunt dissector further includes a spine disposed within said absorbent body of material.

9. A multifunctional tissue dissecting instrument as recited in claim 8 wherein said spine includes a trunk and branches angularly extending from said trunk.

10. A multifunctional tissue dissecting instrument as recited in claim 8 wherein said spine includes a hollow tubular member.

11. A multifunctional tissue dissecting instrument as recited in claim 1 wherein said probe tip is configured as a scissors.

12. A multifunctional tissue dissecting instrument as recited in claim 11 wherein said blunt dissector distal end includes a recess configured to receive and stabilize opposed blades of said scissors.

13. A multifunctional tissue dissecting instrument as recited in claim 1 wherein said probe is detachably coupled with said blunt dissector.

14. A multifunctional tissue dissecting instrument as recited in claim 13 and further comprising a sleeve coupling said probe with said handle, said sleeve being movable relative to said blunt dissector by operation of said handle and having a configuration to mount said probe in a detachable manner.

15. A multifunctional tissue dissecting instrument as recited in claim 13 and further comprising a hub mounting said blunt dissector and a housing mounting said probe, wherein said housing and hub are configured to couple with one another in a detachable manner so that said probe can be removed from said blunt dissector with said housing.

16. A multifunctional tissue dissecting instrument as recited in claim 15 wherein said hub defines a passage between an operating channel in said blunt dissector and at least one of a valve and a coupling mounted by said hub.

17. A multifunctional tissue dissecting instrument as recited in claim 1 wherein said probe is hollow to define an operating channel through said instrument.

18. A multifunctional tissue dissecting instrument as recited in claim 1 wherein said probe is solid.

19. A multifunctional tissue dissecting instrument as recited in claim 1 and further comprising an electrical connector at a proximal end of said instrument, wherein said probe tip is electrically coupled with said connector for use as a cautery.

20. A multifunctional tissue dissecting instrument as recited in claim 1 wherein said probe tip is configured as an L-shaped hook and said blunt dissector distal end includes a recess configured to receive said L-shaped hook when said probe tip is retracted.

21. A multifunctional tissue dissecting instrument as recited in claim 1 wherein said probe tip is configured as a J-shaped hook and said blunt dissector distal end includes a recess configured to receive said J-shaped hook when said probe tip is retracted.

22. A multifunctional tissue dissecting instrument as recited in claim 1 wherein said probe tip is configured as a needle with a sharp, tissue penetrating tip.

23. A multifunctional tissue dissecting instrument for use in a surgical procedure of the type where a portal is established to provide access to an operative site within an anatomical cavity and said instrument is introduced to the operative site through the portal, said multifunctional instrument comprising a blunt dissector having a distal end adapted to be introduced into the anatomical cavity through the portal, a proximal end adapted to be positioned externally of the anatomical cavity, and a dissector body disposed at said distal end to contact anatomical tissue for blunt dissection;

a probe disposed within said blunt dissector and having a tip movable between a retracted position where said probe tip is disposed within said blunt dissector and an extended position where said probe tip protrudes from said distal end of said blunt dissector; and a handle disposed at said proximal end of said blunt dissector and coupled with said probe, said handle being selectively operable to move said probe tip between said retracted and extended positions, whereby said instrument can be used as a blunt dissector when said probe tip is moved to said retracted position and said instrument can be used to treat anatomical tissue with said probe when said probe tip is moved to said extended position;

wherein said probe is hollow to define an operating channel through said instrument and wherein said probe further includes a valve with a coupling.

24. A multifunctional tissue dissecting instrument for use in a surgical procedure of the type where a portal is established to provide access to an operative site within an anatomical cavity and said instrument is introduced to the operative site through the portal, said multifunctional instrument comprising an elongate tubular member having a distal end adapted to be introduced into the anatomical cavity through the portal, a proximal end adapted to be positioned externally of the anatomical cavity and an operating channel extending through said elongate tubular member to provide access to the operative site in the anatomical cavity; and an absorbent body of material disposed at said distal end of said elongate tubular member and having a configuration to absorb body fluids at the operative site and to contact anatomical tissue for blunt dissection without obstructing access to the operative site via said operating channel.

25. A multifunctional tissue dissecting instrument as recited in claim 24 and further comprising a coupling disposed at a proximal end of said operating channel.

26. A multifunctional tissue dissecting instrument as recited in claim 25 and further comprising a hub mounting said proximal end of said elongate tubular member and defining a passage between said operating channel and said coupling.

27. A multifunctional tissue dissecting instrument as recited in claim 24 wherein said absorbent body includes a body of material with a spine disposed therein.

28. A multifunctional tissue dissecting instrument as recited in claim 27 wherein said absorbent body of material is detachably coupled with said elongate tubular member.

29. A multifunctional tissue dissecting instrument as recited in claim 27 wherein said spine includes a trunk and branches extending angularly from said trunk.

30. A multifunctional tissue dissecting instrument as recited in claim 27 wherein said spine is tubular and includes an open proximal end in communication with said operating channel.

31. A multifunctional tissue dissecting instrument as recited in claim 30 wherein said tubular spine is formed of a flexible material capable of stretching to accommodate instruments of various size and shape.

32. A multifunctional tissue dissecting instrument as recited in claim 30 wherein holes are formed in said tubular spine to establish fluid communication between said operating channel and said body of material.

33. A multifunctional tissue dissecting instrument as recited in claim 30 wherein said tubular spine extends through said elongate tubular member to define said operating channel.

34. A multifunctional tissue dissecting instrument as recited in claim 33 wherein a proximal portion said tubular spine is disposed within said elongate tubular member in spaced relation thereto in order to define a gap therebetween for defining at least one additional operating channel.

35. A multifunctional tissue dissecting instrument as recited in claim 34 wherein a distal portion of said tubular spine protrudes from said distal end of said elongate tubular member and said absorbent body of material is disposed around said distal portion of said tubular spine in communication with said at least one additional operating channel.

36. A multifunctional tissue dissecting instrument as recited in claim 35 wherein said absorbent body of material protrudes distally beyond said tubular spine to define a blunt surface.

37. A multifunctional tissue dissecting instrument as recited in claim 35 wherein said gap is used to define a plurality of additional operating channels.

* * * * *